(12) United States Patent
Wright et al.

(10) Patent No.: US 10,328,145 B2
(45) Date of Patent: *Jun. 25, 2019

(54) SCALABLE MANUFACTURING PLATFORM FOR VIRAL VECTOR PURIFICATION AND VIRAL VECTORS SO PURIFIED FOR USE IN GENE THERAPY

(71) Applicant: THE CHILDREN'S HOSPITAL OF PHILADELPHIA, Philadelphia, PA (US)

(72) Inventors: John Fraser Wright, Princeton, NJ (US); Guang Qu, Sicklerville, NJ (US); Bernd Hauck, Hamilton, NJ (US); Katherine A. High, Merion Station, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/081,001

(22) Filed: Mar. 25, 2016

(65) Prior Publication Data

US 2016/0206706 A1 Jul. 21, 2016

Related U.S. Application Data

(63) Continuation of application No. 13/561,753, filed on Jul. 30, 2012, now Pat. No. 9,408,904, which is a continuation-in-part of application No. PCT/US2011/022371, filed on Jan. 25, 2011.

(60) Provisional application No. 61/299,184, filed on Jan. 28, 2010.

(51) Int. Cl.

| | |
|---|---|
| *C07K 2/00* | (2006.01) |
| *C12N 7/00* | (2006.01) |
| *A61K 38/46* | (2006.01) |
| *A61K 39/23* | (2006.01) |
| *A61K 48/00* | (2006.01) |
| *C12N 15/64* | (2006.01) |
| *C12N 15/86* | (2006.01) |
| *C12N 15/864* | (2006.01) |

(52) U.S. Cl.
CPC ............ *A61K 39/23* (2013.01); *A61K 38/465* (2013.01); *A61K 48/0091* (2013.01); *C07K 2/00* (2013.01); *C12N 7/00* (2013.01); *C12N 15/64* (2013.01); *C12N 15/86* (2013.01); *C12N 15/864* (2013.01); *A61K 48/00* (2013.01); *C12N 15/8645* (2013.01); *C12N 2750/14011* (2013.01); *C12N 2750/14051* (2013.01); *C12N 2750/14111* (2013.01); *C12N 2750/14143* (2013.01); *C12N 2750/14151* (2013.01); *C12Y 301/01064* (2013.01)

(58) Field of Classification Search
CPC .. A61K 39/23; A61K 38/465; A61K 48/0091; A61K 48/00; A61K 39/12; A61K 39/235; A61K 39/42; C12N 15/864; C12N 15/64; C12N 7/00; C12N 15/86; C12N 2750/14051; C12N 2750/14011; C12N 15/8645; C12N 2750/14111; C12N 2750/14143; C12N 2750/14151; C12N 15/70; C12N 2750/14061; C12N 2750/14122; C12N 2750/14132; C12N 2750/14171; C12N 2750/14334; C12N 2750/14361; C12N 2750/14311; C07K 2/00; C07K 14/005; C12Y 301/01064

See application file for complete search history.

(56) References Cited

U.S. PATENT DOCUMENTS

| | | | |
|---|---|---|---|
| 6,093,392 | A | 7/2000 | High et al. |
| 6,593,123 | B1 | 7/2003 | Wright et al. |
| 7,261,544 | B2 | 8/2007 | Qu et al. |
| 7,704,721 | B2 | 4/2010 | Wright et al. |
| 7,998,734 | B2 | 8/2011 | High et al. |
| 8,137,948 | B2 | 3/2012 | Qu et al. |
| 2002/0127582 | A1 | 9/2002 | Atkinson et al. |
| 2003/0207439 | A1 | 11/2003 | Wright et al. |
| 2004/0002159 | A1 | 1/2004 | Xiao et al. |
| 2004/0102388 | A1 | 5/2004 | High et al. |
| 2005/0042740 | A1 | 2/2005 | Qu et al. |
| 2006/0035364 | A1 | 2/2006 | Wright et al. |
| 2006/0188483 | A1* | 8/2006 | Rabinowitz ............ C12N 15/86 424/93.2 |
| 2007/0243615 | A1 | 10/2007 | Qu et al. |
| 2011/0076744 | A1 | 3/2011 | Wright et al. |
| 2012/0135515 | A1 | 5/2012 | Qu et al. |

FOREIGN PATENT DOCUMENTS

| | | |
|---|---|---|
| WO | 2005/118792 | 12/2005 |
| WO | 2008/128251 | 10/2008 |
| WO | 2009153563 A1 | 12/2009 |

OTHER PUBLICATIONS

Wright JF. Manufacturing and characterizing AAV-based vectors for use in clinical studies. Gene Ther. Jun. 2008;15(11):840-8.*
Wright JF, Le T, Prado J, Bahr-Davidson J, Smith PH, Zhen Z, Sommer JM, Pierce GF, Qu G. Identification of factors that contribute to recombinant AAV2 particle aggregation and methods to prevent its occurrence during vector purification and formulation. Mol Ther. Jul. 2005;12(1):171-8.*
Ayuso, E. et al., High AVV Vector Purity Resits in Serotype- and Tissue-Independent Enhancement of Transduction Efficiency, Gene Ther., 1010, 17(4):503-10. Epub Dec. 3, 2009.
"bona fide" definition, Merriam-Webster Online Dictionary, retrieved Jun. 18, 2014.

(Continued)

*Primary Examiner* — Rachel B Gill
(74) *Attorney, Agent, or Firm* — Pillsbury Winthrop Shaw Pittman LLP; Robert M. Bedgood (57) ABSTRACT

Methods for preparing highly purified AAV vector formulations are provided. The highly pure AAV formulations described herein are superior for clinical use.

24 Claims, 4 Drawing Sheets

(56) References Cited

OTHER PUBLICATIONS

Chuah, M., et al., Gene Therapy for Hemophilia "A" and "B": Efficacy, Safety and Immune Consequences, Verh K. Acad. Geneeskd Belg., 2007, 69(5-6):315-34.

Favaro, P., et al., Host and Vector-Dependent Effects on the Risk of Germline Transmission of AAV Vectors, Mol. Ther., 2009, 17(6):1022-30. Epub Mar. 17, 2009.

Hauck, B., et al., A Scalable Manufacturing Platform for Purification of AAV Srotypes 2, 5, 6 and 8 for IND-Supporting Pre-Clinical Studies and Clinical Trials, Molecular Therapy, May 17, 2009, suppl. 1:S17 [Abstract].

Hauck, B., et al., Process Characterisation and GMP Manufacture of a Gene Transfer Vector for leber congenital Amaurosis, Molecular Therapy, May 15, 2007, suppl. 1:S167 [Abstract].

Koerber, J.T., et al., Construction of Diverse Adeno-Associated Viral Libraries for Directed Evolution of Enhanced Gene Delivery Vehicles, Nat. Protoc., 2006, 1(2):701-6.

Kronenberg, S., et al., A Conformational Change in the Adeno-Associated Virus Type 2 Capsid Leads to the Exposure of Hidden VP1 N Termini, J. Virol., 2005, 79(9):5296-303.

Maguire, A.M., et al., Safety and Efficacy of Gene Transfer for Leber's Congenital Amaurosis, New England Journal of Medicine, 2008, 358(21):2240-2248.

Maguire, A.M., et aL, Supplement to Safety and Efficacy of Gene Transfer for Leber's Congenital Amaurosis, New England Journal of Medicine, 2008, 358(21):2240-2248.

Maguire, A.M., et al., Slides to the Discussion of Human Gene Transfer Protocol #0510-740#, 102nd Meeting of the Recombinant DNA Advisory Committee (RAC), NIH Office of Biotechnology Activities, Bethesda, Maryland, USA, Dec. 2005, 13:1-49.

Matsushita, T., et al., Adeno-Associated Virus vectors Can be Efficiently Produced Without Helper Virus, Gene Ther., 1998, 5(7):938-45.

Mehlhorn, I., et al., High-level Expression and Characterization of a Purified 142-Residue Polypeptide of the Prion Protein, Biochemistry, 1996, 35(17):5528-37.

"Microfluidizer Protocol", Novatt J. Rout lab Protocol, Mar. 20, 2007 http://commonfund.nih.gov/sites/default/files/Microfluidizer.pdf.

Okada, T., et al., Scalable Purification of Adeno-Associated Virus Serotype 1 (AAV1) and AAV8 Vectors, Using Dual Ion-Exchange Adsorptive Membranes, Hum. Gene Ther., 2009, 20(9):1013-21.

"Protein Concentration and Diafiltration by Tangential Flow Filtration", Technical Brief, Millipore Court, Jun. 2003.

Qu, G., et al., Separation of Adeno-Associated Virus Type 2 Empty Particles from Genome Contaiing Vectors by Anion-Exchange Column Chromatography, J. Virol. Methods, 2007, 140(1-2):183-92. Epub Dec. 28, 2006.

Sun, J., et al., Intraarticular Factor IX Protein or Gene Replacement Protects Against Development of Hemophillic Synovitis in the Absence of Circulating Factor IX, Blood, 2008, 112(12):4532-41. Epub Aug. 20, 2008.

Wright, J.F., Adeno-Associated Virus Vectors to Support Clinical Studies, Presentation at the 11th Annual Meeting of the American Society for Gene Therapy, Boston, MA, USA, May 28, 2008, 5-12. Retrieved from the internet. http://www.gtrp.org/doc/CHOP%20AAV%20Lab_5.28.08.ppt.

Wright, J.F., et al., Identification of Factors that Contribute to Recombinant AAV2 Particle Aggregation and Methods to Prevent its Occurrence During Vector Purification and Formulation, Mol. Ther., 2005, 12(1):171-8.

Wright, J.F., et al., Manufacturing and Regulatory Strategies for Clinical AAV2-hRPE65, Curr. Gene. Ther., 2010, 10 (5):341-9.

Zolotukhin S., et al., Recombinant Adeno-Associated Virus Purification Using Novel Methods Improves Infectious Titer and Yield, Gene Ther., 1999, 6(6):973-85.

Zhou, J., et al., PEG-modulated column chromatography for purification of recombinant adeno-associated virus serotype 9, Journal of Virological Methods, 2011, 173:99-107.

National Intellectual Property Administration, P.R. China, Chinese Office Action for CN 201610109900.9, Nov. 22, 2018, pp. 1-13.

\* cited by examiner

SCALABLE MANUFACTURING PLATFORM FOR VIRAL VECTOR PURIFICATION AND VIRAL VECTORS SO PURIFIED FOR USE IN GENE THERAPY

RELATED APPLICATIONS

This application is a continuation application of application Ser. No. 13/561,753, filed Jul. 30, 2012, which claims the benefit of priority to PCT/US2011/22371, filed Jan. 25, 2011 and provisional application No. 61/299,184, filed Jan. 28, 2010, all of which applications are expressly incorporated herein by reference in their entirety.

GOVERNMENT SUPPORT

Pursuant to 35 U.S.C. § 202(c), it is acknowledged that this invention was made with government support under Grant No. HHSN268200748203C awarded by the National Institutes of Health. The U.S. Government has certain rights in the invention.

FIELD OF THE INVENTION

This invention relates to the fields of good manufacturing practices and viral vector purification. More specifically, the compositions and methods facilitate preparation of highly purified recombinant AAV for use in gene therapy protocols.

BACKGROUND OF THE INVENTION

Several publications and patent documents are cited throughout the specification in order to describe the state of the art to which this invention pertains. Each of these citations is incorporated herein by reference as though set forth in full.

Gene delivery is a promising method for the treatment of acquired and inherited diseases. A number of viral-based systems for gene transfer purposes have been described, including adeno-associated virus (AAV)-based systems. AAV is a helper-dependent DNA parvovirus that belongs to the genus Dependovirus. AAV requires co-infection with an unrelated helper virus, e.g., adenovirus, herpes virus, or vaccinia, in order for a productive infection to occur. In the absence of a helpervirus, AAV establishes a latent state by inserting its genome into a host cell chromosome. Subsequent infection by a helper virus rescues the integrated viral genome, which can then replicate to produce infectious viral progeny.

AAV has a wide host range and is able to replicate in cells from any species in the presence of a suitable helper virus. For example, human AAV will replicate in canine cells co-infected with a canine adenovirus. AAV has not been associated with any human or animal disease and does not appear to alter the biological properties of the host cell upon integration. For a review of AAV, see, e.g., Berns and Bohenzky (1987) Advances in Virus Research (Academic Press, Inc.) 32:243-307.

The construction of infectious recombinant AAV (rAAV) virions has been described. See, e.g., U.S. Pat. Nos. 5,173,414 and 5,139,941; International Publication Numbers WO 92/01070 (published Jan. 23, 1992) and WO 93/03769 (published Mar. 4, 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; and Kotin, R. M. (1994) Human Gene Therapy 5:793-801.

AAV vectors can be engineered to carry a heterologous nucleotide sequence of interest (e.g., a selected gene encoding a therapeutic protein, an antisense nucleic acid molecule, a ribozyme, a miRNA or the like) by deleting, in whole or in part, the internal portion of the AAV genome and inserting the DNA sequence of interest between the ITRs. The ITRs remain functional in such vectors allowing replication and packaging of the rAAV containing the heterologous nucleotide sequence of interest. The heterologous nucleotide sequence is also typically linked to a promoter sequence capable of driving gene expression in the patient's target cells under the certain conditions. Termination signals, such as polyadenylation sites, can also be included in the vector.

While completely eliminating immunogenicity of a viral vector is not a realistic goal, minimizing immunogenicity of AAV vectors prepared for human gene therapy is highly desirable. It is an object of the present invention to provide compositions and methods which achieve this objective.

SUMMARY OF THE INVENTION

In accordance with the present invention, a method for purifying bona fide AAV vector particles comprising a transgene encoding a therapeutic protein or fragment thereof from an AAV preparation comprising AAV vector particles, empty capsids and host cell impurities, thereby providing an AAV product substantially free of AAV empty capsids is provided. Also provided are empty capsids purified using the method described herein. An exemplary purification scheme comprises harvesting cells transduced with AAV; concentrating the cells via Tangential Flow Filtration; and lysing the cells by microfluidization to form a lysate. The lysate is then filtered and clarified. Following clarification, the AAV particles are purified by ion exchange column chromatography and optionally further concentrated by tangential flow filtration. The eluate so generated is then added to an isopynic gradient and subjected to ultracentrifugation, the layer containing the viral particles is harvested and subjected to buffer exchange by Tangential Flow Filtration. The purified AAV particles are then formulated with surfactant and the resulting formulation filtered to remove any remaining impurities there by producing a highly purified AAV product, wherein said bona fide AAV vector particles are present in said AAV product in an amount of at least 95%, preferably at greater than 98%.

In a preferred embodiment, the AAV product comprises AAV particles at a concentration of $10^{15}$ particles per mL, more preferably the particles are present at a concentration of $10^{16}$ particles per mL and most preferably, the particles are present at a concentration of $10^{17}$ particles per mL.

The AAV vectors so purified may be of a variety of serotypes, including without limitation, AAV1, AAV2, AAV5, AAV6, AAV8 and AAV9.

In yet another embodiment an AAV vector formulation comprising AAV particles purified using the method described above in a pharmaceutically acceptable carrier is disclosed.

The purified AAV particles of the invention comprise a heterologous nucleic acid encoding a desirable gene product. Such products include without limitation, siRNAs, antisense molecules, miRNAs, ribozymes and the like. Other products include nucleic acids encoding hormones, growth receptors, ligands and proteins useful for correction of inborn errors of metabolism. In a particularly preferred embodiment, the vector encodes a protein selected from the group consisting of RPE65, Factor VIII and Factor IX.

Highly purified empty capsid fractions can also be obtained using the purification methods described herein. Such empty capsid fractions can be employed in anti-AAV binding assays, such as ELISA.

DETAILED DESCRIPTION OF THE INVENTION

The current invention provides an AAV vector purification platform that includes two unique features that distinguish it from current 'industry-standard' scalable AAV vector purification processes: 1) a modular platform process that can be used for purification of different AAV serotypes/capsid variants that provides high vector purity, including efficient removal of vector-related impurities; and 2) a unique sequence of process steps (including a critical 'core' sequence of column chromatography followed by tangential flow filtration, followed by gradient ultracentrifugation) that confers unexpected scalability to the important ultracentrifugation step.

Optimization of AAV vector generation and purification methods ensures that the vector product can efficiently deliver its genetic payload to target cells, and minimizes the potential for activation of deleterious immune responses. Because vector-related impurities are non-self and immunostimulatory with respect to a prospective human recipient, they should be minimized or eliminated during purification of human parenteral products. Vector-related impurities are typically produced in much higher amounts than bona fide vectors during vector generation in cell culture, and are difficult to separate from vectors during purification because they are similar in structure. In crude cell harvests following vector generation, vector-related impurities generally represent >50%, typically ~80%, and may represent >80% of the total AAV particles that are biosynthesized. This has been observed using each of the cell culture systems developed to date to generate AAV vectors. Development of manufacturing processes to purify recombinant AAV as a product to treat human disease must achieve the following objectives: 1) consistent vector purity, potency and safety; 2) manufacturing process scalability; and 3) acceptable cost of manufacturing. Current 'industry standard' scalable AAV vector purification processes do not adequately achieve removal of vector-related impurities, which is important to meet the first objective listed above (consistent vector purity, potency and safety). Moreover, failure to adequately remove vector-related impurities using current industry-standard scalable purification processes has occurred because: 1) development of purification processes of viral products such as recombinant AAV for applications other than vaccines (in which an immune response is typically sought rather than avoided) is relatively immature; 2) many groups involved in the development of scalable purification processes for AAV vectors have been unaware of the high levels of vector-related impurities and/or have assumed that such impurities will not contribute to a clinically significant augmentation of vector immunogenicity; and 3) it is technically challenging to develop scalable purification processes to separate bona fide vectors from vector-related impurities because these AAV particles closely resemble each other with respect to the physico-chemical features (e.g. particle size, and particle surface molecular topology and electrostatic charge distribution) that are typically exploited to achieve purification of biological molecules in scalable process steps.

The following definitions are provided to facilitate the practice of the present invention.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By an "AAV vector" is meant a vector derived from an adeno-associated virus serotype, including without limitation, AAV-1, AAV-2, AAV-3, AAV-4, AAV-5, AAV-6, AAV-7 and AAV-8. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging. Also by an 'AAV vector' is meant the protein shell or capsid, which provides an efficient vehicle for delivery of vector nucleic acid to the nucleus of target cells.

"AAV helper functions" refer to AAV-derived coding sequences which can be expressed to provide AAV gene products that, in turn, function in trans for productive AAV replication. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) J. Virol. 63:3822-3828; and McCarty et al. (1991) J. Virol. 65:2936-2945. A number of other vectors have been described which encode Rep and/or Cap expression products. See, e.g., U.S. Pat. Nos. 5,139,941 and 6,376,237.

The term "vector-related impurities" refers to all types of AAV particles other than bona fide recombinant AAV particles. Vector-related impurities include empty AAV capsids (also referred to as "empties", or "empty particles", and AAV particles containing polynucleotide sequences other than the intended vector genome (also referred to "AAV-encapsidated nucleic acid impurities" or "AAV-encapsidated DNA impurities").

The term "accessory functions" refers to non-AAV derived viral and/or cellular functions upon which AAV is dependent for its replication. Thus, the term captures proteins and RNAs that are required in AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus.'

The term "accessory function vector" refers generally to a nucleic acid molecule that includes nucleotide sequences providing accessory functions. An accessory function vector can be transfected into a suitable host cell, wherein the vector is then capable of supporting AAV virion production in the host cell. Expressly excluded from the term are infectious viral particles as they exist in nature, such as adenovirus, herpesvirus or vaccinia virus particles. Thus, accessory function vectors can be in the form of a plasmid, phage, transposon or cosmid. In particular, it has been demonstrated that the full-complement of adenovirus genes are not required for accessory helper functions. For example, adenovirus mutants incapable of DNA replication and late gene synthesis have been shown to be permissive for AAV replication. Ito et al., (1970) J. Gen. Virol. 9:243; Ishibashi et al, (1971) Virology 45:317. Similarly, mutants within the E2B and E3 regions have been shown to support AAV replication, indicating that the E2B and E3 regions are probably not involved in providing accessory functions. Carter et al., (1983) Virology 126:505. However, adenoviruses defective in the E1 region, or having a deleted E4 region, are unable to support AAV replication. Thus, E1A and E4 regions are likely required for AAV replication, either directly or indirectly. Laughlin et al., (1982) J. Virol. 41:868; Janik et al., (1981) Proc. Natl. Acad. Sci. USA 78:1925; Carter et al., (1983) Virology 126:505. Other characterized Ad mutants include: E1B (Laughlin et al. (1982), supra; Janik et al. (1981), supra; Ostrove et al., (1980) Virology 104:502); E2A (Handa et al., (1975) J. Gen. Virol. 29:239; Strauss et al., (1976) J. Virol. 17:140; Myers et al., (1980) J. Virol. 35:665; Jay et al., (1981) Proc. Natl. Acad. Sci. USA 78:2927; Myers et al., (1981) J. Biol. Chem. 256:567); E2B (Carter, Adeno-Associated Virus Helper Functions, in I CRC Handbook of Parvoviruses (P. Tijssen ed., 1990)); E3 (Carter et al. (1983), supra; and E4 (Carter et al. (1983), supra; Carter (1995)).

Although studies of the accessory functions provided by adenoviruses having mutations in the E1B coding region have produced conflicting results, Samulski et al., (1988) J. Virol. 62:206-210, recently reported that E1B55k is required for AAV virion production, while E1B19k is not. In addition, International Publication WO 97/17458 and Matshushita et al., (1998) Gene Therapy 5:938-945, describe accessory function vectors encoding various Ad genes. Particularly preferred accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such vectors are described in International Publication No. WO 01/83797.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.'

The terms "recombinant AAV virion," "rAAV virion," "AAV vector particle," "full capsids," and "full particles" are defined herein as an infectious, replication-defective virus including an AAV protein shell, encapsidating a heterologous nucleotide sequence of interest which is flanked on both sides by AAV ITRs. A rAAV virion is produced in a suitable host cell which has had sequences specifying an AAV vector, AAV helper functions and accessory functions introduced therein. In this manner, the host cell is rendered capable of encoding AAV polypeptides that are required for packaging the AAV vector (containing a recombinant nucleotide sequence of interest) into infectious recombinant virion particles for subsequent gene delivery.

The terms "empty capsid," and "empty particle," refer to an AAV virion that includes an AAV protein shell but that lacks in whole or part the polynucleotide construct comprising the heterologous nucleotide sequence of interest flanked on both sides by AAV ITRs. Accordingly, the empty capsid does not function to transfer the gene of interest into the host cell. However, the highly purified empty capsid formulations may have utility in other assays, such as ELISA.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties into suitable host cells.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

A stock or preparation of rAAV virions comprising AAV vector particles (packaged genomes) is "substantially free of" AAV empty capsids when at least about 50%-99% or more of the virions present in the stock are rAAV virions with packaged genomes (i.e., AAV vector particles). Preferably, the AAV vector particles comprise at least about 75% to 85%, more preferably about 90% of the virions present in the stock, even more preferably at least about 95%, or even 99% or more by weight of the virions present in the stock, or any integer between these ranges. Thus, a stock is substantially free of AAV empty capsids when from about 40% to about 1% or less, preferably about 25% to about 15% or less, more preferably about 10% or less, even more preferably about 5% to about 1% or less of the resulting stock comprises empty capsids.

A stock or preparation of rAAV virions comprising AAV vector particles (packaged genomes) is "substantially free of" AAV-encapsidated nucleic acid impurities" when at least about 90-99% or more of the virions present in the stock are rAAV virions with packaged bona fide genomes (i.e., AAV vector particles). Preferably, the AAV vector particles comprise at least about 95% to 98%, more preferably about 99% of the virions present in the stock, even more preferably at least about >99% or more by weight of the virions present in the stock, or any integer between these ranges. Thus, a stock is substantially free of AAV-encapsidated nucleic acid impurities when from about 10% to about 1% or less, preferably about 2% or less, more preferably about 1% or less, even more preferably about 0.5% or less of the resulting stock comprises AAV-encapsidated nucleic acid impurities.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil-, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, Buracil-5-oxyacetic acid methylester, uracil-5-oxyacetic acid, pseudouracil, queosine, 2-thiocytosine, and 2,6-diaminopurine.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters."

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

The transgene comprising the heterologous nucleic acid can encode a number of useful products. These can include siRNA, antisense molecules, and miRNAs for example. Alternatively, transgenes can encode hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), any one of the transforming growth factor β superfamily, including TGFβ, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-17, monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors single chain T cell receptors, class I and class II MHC molecules, as well as engineered immunoglobulins and MHC molecules. Useful gene products also include regulatory proteins such as complement regulatory proteins, membrane cofactor protein (MCP), decay accelerating factor (DAF), CR1, CF2 and CD59.

Other useful gene products include those that can correct in born errors of metabolism. Such transgenes can encode for example, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor V, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

The present invention involves reducing the numbers of, or eliminating, AAV vector related impurities (e.g. empty capsids and AAV-encapsidated nucleic acid impurities) contained within purified stocks of AAV virions, with minimal loss to AAV vector particles contained therein. The methods of the present invention may be used regardless of the process in which rAAV virions are generated.

There are several methods that are well known in the art for generating rAAV virions: for example, transfection using vector and AAV helper sequences in conjunction with coinfection with one of the AAV helper viruses (e.g., adenovirus, herpesvirus, or vaccinia virus) or transfection with a recombinant AAV vector, an AAV helper vector, and an accessory function vector. For detailed descriptions of methods for generating rAAV virions see, U.S. Pat. Nos. 6,001,650 and 6,004,797, both incorporated herein by reference in their entireties.

Purification of rAAV Virions

Following recombinant AAV replication (i.e. vector generation in cell culture systems), rAAV virions can be purified from the host cell using a variety of conventional purification methods, such as column chromatography, CsCl gradients, and the like. For example, a plurality of column purification steps can be used, such as purification over an anion exchange column, an affinity column and/or a cation exchange column. See, for example, International Publication No. WO 02/12455. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

Recombinant AAV vectors containing any number of reporter genes can be used to determine infectious titers. For example, alkaline phosphatase, beta-galactosidase (LacZ), green fluorescent protein, or luciferase may be used. After harvesting the transfected host cell, a lysate is formed by disrupting the transfected host cells using techniques suitable for large-scale production, such as microfluidization. The lysate is then filtered (for example, through a 0.45 μm filter), and purified using column chromatographic methods as described herein. Other techniques have also been reported to determine the infectious titer of any AAV vector. See, e.g., Zhen et al., "An Infectious Titer Assay for Adeno-associated Virus (AAV) Vectors with Sensitivity Sufficient to Detect Single Infectious Events." Hum. Gene Ther. (2004) 15:709-715. The clarified cell lystate is subjected to one or more purification process step(s) to purify AAV particles (including bona fide vectors and vector-related impurities) using column chromatography techniques. In preferred methods, the AAV particles are purified using one or more sequential steps involving cation and/or anion exchange chromatography. In a particularly preferred method of the invention, rAAV preparations are obtained by lysing transfected cells to obtain a crude cell lysate by readily scalable methods. The crude cell lysate can then be clarified to remove cell debris by techniques well known in the art, such as filtering, centrifuging, and the like, to render a clarified cell lysate. The crude cell lysate or clarified cell lysate, which contain both AAV particles (bona fide AAV vectors, AAV empty capsids, and AAV vector related impurities) and a range of non AAV vector related impurities, e.g., soluble cellular components from the infected host cell. These can include undesirable cellular proteins, lipids, and/or nucleic acids, and cell culture medium components (e.g. bovine serum), The lysate, is applied to a first cation exchange column. The first cation exchange column functions to further separate the AAV particles from cellular and other components present in the cell lysate preparation. Methods for performing the initial purification of the cell lysate are known. One representative method is described in U.S. Pat. No. 6,593,123, incorporated herein by reference in its entirety.

The use of column chromatography can achieve efficient purification of AAV particles from most other impurities present in the crude harvest following recombinant AAV vector generation in cell culture. For example, one or more ion exchange chromatography steps may be used in sequence to progressively separate AAV particles from impurities. Anion and cation exchange chromatography resins, and other types of chromatography resins, may be used in various combinations, with varying combinations being optimal depending on the specific AAV serotype of interest. Use of the following chromatography resins in a single chromatography step for purification of the following recombinant AAV serotypes can be used:

dextran, polyacrylate, polyvinyl, polystyrene, silica and polyether matrices; and composites. Particularly preferred herein are matrices containing the functional ligand R—$SO_3^-$, preferably sulfopropyl or sulfoethyl resins. Representative matrices include but are not limited to POROS HS, POROS SP, POROS S (all strong cation exchangers available from Applied Biosystems, Foster City, Calif.), POROS CM (weak cation exchanger available from Applied Biosystems, Foster City, Calif.), TOSOHAAS TOYOPEARL SP550C and MERCK FRACTOGEL EMD $SO_3$-650 (m), as well as SOURCE 15S, SOURCE 30S, SEPHAROSE SP FF, SEPHAROSE SP XL (all available from Amersham Bioscience, Piscataway, N.J.).

For all column chromatography protocols given below, columns can be prepared using standard protocols known in the art with the appropriate buffer solutions. Sample is then loaded. For the first cation exchange column used, conditions are such that all AAV particles bind to the column resin and are subsequently eluted together, but are separated from other cellular components and debris present in the cell lysate. For example, AAV particles are eluted using a buffer of appropriate ionic strength. Suitable buffers include e.g., 10-50 mM sodium phosphate, preferably 15-40, such as 15, 20, 25, 30, 35, 40, etc. mM sodium phosphate containing salt, such as NaCl or KCl, at a concentration of e.g, 100-700 mM, such as 200-400 mM, e.g., 200, 300, 325, 350, 370, 380, 400, etc., or any concentration within these ranges. The

| Resin | Order Information | Reference | AAV serotype |
|---|---|---|---|
| Poros 50HS | Applied Biosystems, PN 1-3359-07 | http://www3-appliedbiosystems-com/cms/groups/psm_support/documents/generaldocuments/cms_041648-pdf | AAV2 AAV6 |
| Poros 50HQ | Applied Biosystems, PN 1-2559-07 | http://www3-appliedbiosystems-com/cms/groups/psm_support/documents/generaldocuments/cms_041639-pdf | AAV1 AAV8 |
| Poros 50PI | Applied Biosystems, PN 1-2459-07 | http://www3-appliedbiosystems-com/cms/groups/psm_support/documents/generaldocuments/cms_041639-pdf | AAV5 |
| CHT Ceramic Hydroxy-apatite | BioRad PN 1570041 | http://www-bio-rad-com/webroot/web/pdf/psd/literature/LIT611E-PDF | AAV9 |

In some case, two or more sequential chromatography steps may be useful to achieve higher AAV particle purity and assure removal of adventitious viral contaminants, a requirement for the manufacture of recombinant AAV for use in human subjects to treat diseases. Sequential chromatography steps can use different resins performed sequentially in varying orders, optimized for different recombinant AAV serotypes. For example, vector particle purification achieved by two sequential chromatography steps may employ the following format:

| First step | Anion | Anion | Cation | Cation |
|---|---|---|---|---|
| Second step | Anion | Cation | Cation | Cation |

Suitable cation exchangers for both the first cation exchange column and the second cation exchange column, if used, include a wide variety of materials known in the art. Particularly preferred are strong cation exchangers capable of binding rAAV virions over a wide pH range. For example carboxymethylated and sulfonated cation exchange matrices are particularly useful for use herein. Useful matrix materials include but are not limited to, cellulose matrices, such as fibrous, microgranular and beaded matrices; agarose, pH of the buffer can be from about 3 to about 9.5, such as 4-8, e.g., pH 4, 4.5, 5, 5.5, 6, etc., or any pH within these ranges. The fractions are collected and then can be run either on an anion exchange column and/or a second cation exchange column under separating conditions.

If a second cation exchange column is used to further purify AAV particles in a subsequent step, two elution buffers may be used, one low salt buffer and one high salt buffer. In particular, additional impurities are separated from AAV particles using an appropriate buffer at a pH of from about pH 6 to pH 12, preferably pH 7 to pH 10, and even more preferably pH 7.5 to pH 9.5, such as pH 7.5, 8.0, 8.1, 8.2, 8.3, 8.4, 8.5, 9.0, 9.1, 9.2, 9.3, 9.4, 9.5, or any pH between the stated ranges. Appropriate buffers are well known in the art and include, without limitation, buffers with the following buffer ions: acetic acid; malonic acid; MES; phosphate; HEPES, BICINE, and the like. To elute the sample, the ionic strength of the starting buffer is increased using a salt, such as NaCl, KCl, ammonia sulfate or any other salts containing sulfate, formate, acetate, citrate, and/or phosphate. In one embodiment of the invention, the column is first treated with a low salt concentration, e.g., 10-200 mM of ammonium acetate, such as 20, 25, 30, 35, 40, 45, 50, 55, 60, 65-100 mM, or any concentration within these ranges. This treatment results in elution of AAV vector particles from the column resin. Subsequently the column is treated with a higher salt concentration in order to elute AAV empty capsids. One example for use as the second buffer is ammonium acetate with a concentration of 100-800 mM, preferably 500-700 mM, such as 500, 550, 600, 650, 700, 800 mM, or any concentration within these stated ranges. Using these conditions, the AAV vector particles elute in the early fractions and the empty particles later.

As explained above, in an alternate method of the invention, the preparation from the first cation exchange column is applied to an anion exchange column either in place of or in addition to the second cation exchange column. If an anion exchange column is used in addition to the second cation exchange column, it can be used either prior or subsequent to the second cation exchange column. Moreover, a second anion exchange column can be used after the first anion exchange column. A number of suitable anion exchangers for use with the present invention are known and include without limitation, MACRO PREP Q (strong anion-exchanger available from BioRad, Hercules, Calif.); UNO-SPHERE Q (strong anion-exchanger available from BioRad, Hercules, Calif.); POROS 50HQ (strong anion-exchanger available from Applied Biosystems, Foster City, Calif.); POROS 50D (weak anion-exchanger available from Applied Biosystems, Foster City, Calif.); POROS 50PI (weak anion-exchanger available from Applied Biosystems, Foster City, Calif.); SOURCE 30Q (strong anion-exchanger available from Amersham Biosciences, Piscataway, N.J.); DEAE SEPHAROSE (weak anion-exchanger available from Amersham Biosciences, Piscataway, N.J.); Q SEPHAROSE (strong anion-exchanger available from Amersham Biosciences, Piscataway, N.J.).

The anion exchange column is first equilibrated using standard buffers and according to the manufacturer's specifications. For example, the column can be equilibrated with, e.g., a 5 to 50 mM, preferably 7-20 mM, such as 10 mM, sodium phosphate buffer. Sample is then loaded and two elution buffers are used, one low salt buffer and one high salt buffer. Fractions are collected following each of the low salt and high salt washes and protein is detected in the fractions using standard techniques, such as monitoring UV absorption at 260 and 280 nm. Using an anion exchanger, the protein peaks from the lower salt eluate contain AAV empty capsids and the higher salt fractions contain AAV vector particles.

In particular, on the anion exchange column, AAV particles can be further purified using an appropriate buffer at a pH of from about pH 5 to pH 12, preferably pH 6 to pH 10, and even more preferably pH 7 to pH 9.5, such as pH 7.1, 7.2, 7.3, 7.4-8.0, 8.1, 8.2, 8.3, 8.4, 8.5-9.0, 9.1, 9.2, 9.3, 9.4, 9.5, or any pH between the stated ranges. Appropriate buffers for use with the anion exchange columns are well known in the art and are generally cationic or zwitterionic in nature. Such buffers include, without limitation, buffers with the following buffer ions: N-methylpiperazine; piperazine; Bis-Tris; Bis-Tris propane; Triethanolamine; Tris; N-methyldiethanolamine; 1,3-diaminopropane; ethanolamine; acetic acid, and the like. To elute the sample, the ionic strength of the starting buffer is increased using a salt, such as NaCl, KCl, sulfate, formate or acetate, at an appropriate pH.

In one embodiment of the invention, the anion exchange column is first treated with a low salt concentration, e.g., 10-100 mM of NaCl, such as 10, 20, 25, 30, 35, 40, 45, 50, 55, 60, 65-100 mM, or any concentration within these ranges. Following initial treatment, the column is then treated with a higher salt concentration in order to elute impurities, such as a higher NaCl concentration, or with another buffer with a greater ionic strength. One example for use as the second buffer is a sodium acetate buffer or a Tris-based buffer with a concentration of 100-300 mM, preferably 125-200 mM, such as 125, 130, 140, 150, 160, 170, 180, 190, 200 mM, or any concentration within these stated ranges. After additional impurities are eluted from the column, the AAV particles can be recovered using a higher concentration of salt. One example for use as the elution buffer is 10 mM Tris buffer containing sodium acetate at a concentration in the range of 100-500 mM, preferably 130-300 mM, such as 100, 130, 150, 200, 250, 300, 350, 400, 450, 500 mM, or any concentration within these stated ranges.

The use of cation or anion exchange chromatography resins, the nature of the resins used (i.e. strong or weak ion exchangers) and the conditions of salt concentration, buffer used, and pH, will vary on the AAV capsid variant (i.e. AAV capsid serotype or pseudotype). While the known AAV capsid variants all share features such as size and shape, they differ in fine details of molecular topology and surface charge distribution. Hence, while all capsid variants are expected to be amenable to purification by ion exchange chromatography, and relevant methods can be determined in a systematic manner using chromatography resin and buffer screening experiments, different conditions will be required for each AAV capsid variant to achieve efficient AAV particle purification. Such conditions are readily apparent to the skilled artisan.

Column chromatography steps are well suited to efficiently purify molecular species that share a common molecular shape and similar charge distribution away from other species (e.g. impurities) that have different molecular shapes and charge distributions. In the case of recombinant AAV vectors, which are made in a production cell culture system, a known characteristic of the crude biosynthetic harvest is that numerous types of AAV particles are present therein. These diverse particles include bona fide AAV vector (i.e. a vector capsid containing the intended DNA fragment inside); empty capsids (i.e. a vector capsid with nothing inside), and other vector related impurities (e.g. vector capsids with other (unintended) pieces of DNA inside. In addition to these diverse AAV particles (i.e. bona fide vectors and vector related impurities), other types of impurities (e.g., host cell proteins, lipids and/or nucleic acid and/or cell culture medium components) are present in abundance. Column chromatography is especially well suited to purify AAV particles from the undesirable impurities. Gradient ultracentrifugation, though difficult to perform with large volumes of material, is well suited to separating most AAV vector-related impurities from bona fide AAV vectors, based on differences in densities of these respective particles. Gradient ultracentrifugation has to date generally been considered not scalable, and therefore heretofore not an appropriate manufacturing process step for use in large scale manufacturing processes. This perceived non-scalability of the gradient ultracentrifugation step is due in part to the requirement in the art to process relatively large volumes material to recover relatively small amounts of recombinant AAV. However, AAV particles that have already been purified by one or more column chromatography steps as described above can be efficiently concentrated by tangential flow filtration, for example using a hollow fiber membrane with a nominal pore size corresponding to a 100 kDa molecular weight cutoff, to high concentration so that large amounts of vector can be prepared on a single standard ultracentrifugation run, which can handle approximately 400 mL of solution containing purified vector particles. For example, chromatography-purified AAV particles containing 10% bona fide AAV vectors (and therefore 90% vector-related impurities such as empty capsids) can be concentrated to $10^{14}$ particles per mL (containing $10^{13}$ AAV vector particles per mL and $9 \times 10^{13}$ particles per mL of vector related impurities), can be processed in a single ultracentrifugation run, e.g., ~400 mL per batch using a Beckman Ti50 Rotor resulting in approximately $4 \times 10^{15}$ bona fide AAV vector particles ($10^{13}$ vg/mL $\times$ 400 mL=$4 \times 10^{15}$ vg). This yield of AAV vector is sufficient to provide many doses for many clinical applications, achieving efficient separation of the AAV vector particles from the majority of AAV vector-related impurities. For clinical applications requiring higher doses of vector, purified AAV particles containing 10% bona fide AAV vectors can be concentrated to $10^{15}$ particles per mL by tangential flow filtration (TFF), and can then be processed in a single ultracentrifugation run to result in approximately $4 \times 10^{16}$ vector genomes (bona fide AAV vectors). For other clinical applications that require even greater doses of vector, purified AAV particles containing 10% bona fide AAV vectors can be concentrated to $10^{16}$ particles per mL by TFF, and can then be processed in a single ultracentrifugation run to result in approximately $4 \times 10^{17}$ vector genomes (bona fide AAV vectors). Concentration of purified AAV particles to $10^{16}$ particles per mL is feasible. This corresponds to a mass concentration of approximately 100 milligrams per milliliter, a concentration that can be achieved for other purified biological molecules such as monoclonal antibodies. Such high concentrations require appropriate attention to formulation to avoid unwanted stability issues such as aggregation (Wright et al, 2005). The novel combination of purification of AAV particles from clarified host cell lysates by column chromatography, concentration (if necessary) of purified AAV particles by known scalable manufacturing steps such as tangential flow filtration, combined with isopynic gradient ultracentrifugation provides large amounts of highly purified recombinant AAV vector. The use of gradient ultracentrifugation provides for greater flexibility (e.g., applicability to vectors derived from various AAV serotypes) and purity (e.g., efficient removal of vector related impurities), critical considerations for cost effectiveness and long term efficacy in human clinical applications. The combination of efficient column chromatography and tangential flow filtration, both readily scalable, biopharmaceutical industry standard manufacturing process steps, render the subsequent density gradient ultracentrifugation step scalable. The novel combination of these steps, performed as outlined above, provides a purification platform generally applicable to all AAV capsid variants that is flexible, scalable, and critically, provides sufficiently high purity (i.e. absence of general impurities as well as vector related impurities) to significantly enhance gene transfer efficiency and minimize the probability of efficacy limiting host immune responses following administration to human subjects for gene therapy.

Methods for assaying for empty capsids and AAV vector particles with packaged genomes are known in the art. See, e.g., Grimm et al., Gene Therapy (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., J. Virol. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit.

To test for infectious titer, the methods include the seeding of about 100,000 host cells, preferably of human origin, most preferably HeLa cells, into tissue culture-treated plates, preferably 24-well tissue culture-treated plates, and incubated for about 24 hours after which adenovirus, preferably the adenovirus-2 serotype, and treated rAAV stock is added to the host cells. The host cells, adenovirus, and rAAV stock are allowed to incubate for 24 hours, after which the host cells are fixed, preferably with formaldehyde and glutaraldehyde, and stained with an appropriate agent that will detect the rAAV expressed transgene; for example, with rAAV-LacZ, X-gal is contemplated as the staining agent. Other agents for other reporter genes are well known in the art. More general methods to determine infectivity titers of vectors containing any transgene are also known in the art. See, e.g., Zhen et al., (2004) "An Infectious Titer Assay for Adeno-associated Virus (AAV) Vectors with Sensitivity Sufficient to Detect Single Infectious Events." Hum. Gene Ther. (2004) 15:709-715.

Virus based vectors offer a great benefit for therapeutic gene transfer because they confer a high degree of efficiency for gene delivery to target cells relative to non viral methods. However, an inherent risk when using virus based vectors is the potential for immunotoxicity. All viral antigens are known to provoke immune responses of different types and of variable severity. For example, in humans that are exposed to them, such antigens and cells associated with these antigens becoming the target of immune effector functions such as antibodies and cytotoxic T lymphocytes. Among known viruses, AAV is one of the least immunogenic, with the least potential for significant immunotoxicity, providing a recognized benefit in connection with administration of gene transfer vectors. However, AAV capsid protein still represents a source of viral antigen that may provoke an unwanted immune response. It is reasonable to assume that the severity of immunotoxicity caused by the AAV capsid protein in a human subject who receives an AAV vector will be proportional to the amount of AAV capsid protein administered. Therefore, a higher dose of AAV capsid can be correlated to a higher risk of significant immunotoxicity. To ensure the safest use of such vectors for administration to human subjects, the amount of AAV capsid protein associated with an efficacious dose of vector genomes should be minimized. Methods of purifying AAV vectors that efficiently remove vector-related impurities, especially AAV empty capsids that typically represent 50-90%, and can represent >90% of AAV particles generated in typical cell culture vector production, will significantly reduce the risk of immunotoxicity in a human recipient. It was reported that a human recipient that received a dose (hepatic administration) of $2 \times 10^{12}$ vg/kg (total body weight)

of recombinant AAV vectors that were substantially free of vector related impurities (i.e. essentially empty capsid free vector) experienced significant, moderate, self limiting immunotoxicity as indicated by elevated liver enzymes starting approximately 3 weeks following vector administration (Manno et al, 2006, Nature Medicine). Evaluation supported that the nature of this modest and transient immunotoxicity was the induction of AAV capsid-specific cytotoxic T lymphocytes (CTLs) that eliminated hepatocytes expressing AAV capsid-derived peptides (Manno et al, 2006, Nature Medicine). If the same vector genome dose ($2 \times 10^{12}$ vg/kg) of recombinant AAV was prepared using a method that did not substantially remove vector-related impurities (e.g. approximately 80% of the AAV particles in the vector preparation were empty capsids), such a preparation would like be associated with increased severe immunotoxicity as indicated by markedly higher liver enzymes.

The purification method described herein provides vectors with an improved safety profile via efficient removal of vector related impurities (such as empty capsids) in a manner that is scalable, i.e. preparation of large amounts of AAV vectors in a cost effective manner is now possible.

The following examples are provided to illustrate certain embodiments of the invention. They are not intended to limit the invention in any way.

EXAMPLE I

This process has been scaled up for AAV vectors for six common and clinically promising AAV serotypes (AAV1, AAV2, AAV5, AAV6, AAV8, and AAV9). This purification process appears to be applicable to purification of vectors based on most, if not all, AAV serotypes and capsid variants. For each serotype or capsid variant, the details of the column chromatography will vary (i.e. the identity of the chromatography resin and particular conditions of AAV particle purification). The Table below provides resins that have been used successfully to achieve purification of AAV particles as a function of AAV serotype.

Therapy) or other buffer conditions as necessary to prevent particle aggregation. Next, a laboratory scale cesium chloride gradient ultracentrifugation step is performed, for example using a Ti50 rotor containing 12 tubes each containing ~40 mL. This step effectively separates bona fide AAV vectors from most vector-related and other non vector related residual impurities. In this combination and sequence of process steps, including the critical core sequence of: 1) column chromatography; 2) concentration by tangential flow filtration (used if necessary to reduce the volume of vector-containing column eluate); and 3) gradient ultracentrifugation, scalable, efficient, orthogonal purification of vector is achieved. Configured in this order, $>1 \times 10^{15}$ highly purified AAV vectors are routinely separated from vector-related impurities in a single laboratory scale ultracentrifugation run.

Based on reasonable protein concentration loading in cesium chloride in conjunction with the difference in density between bona fide AAV vectors and the majority of vector-related impurities, we predict $4 \times 10^{16}$ AAV vectors can be efficiently separated from vector-related impurities in a single laboratory scale ultracentrifugation run, and at least 10-fold higher amounts separated per run using large-scale ultracentrifugation equipment. As used herein the phrase "bona fide AAV vector" refers to vectors comprising the transgene of interest which are capable of infecting target cells. The phrase excludes empty vectors, and vectors lacking full inserts or those vectors containing host cell nucleic acids. Therefore the centrifugation step is scalable and not limiting for commercial scale manufacturing of many foreseeable AAV vector products to treat human diseases. Assuming the laboratory scale ultracentrifugation (i.e. approximately 400 mL of column purified AAV particles), and concentration by tangential flow filtration of column purified AAV particles to a concentration of $1 \times 10^{15}$ AAV particles per milliliter (containing $1 \times 10^{14}$ bona fide AAV vectors per milliliter), the following numbers of doses could be prepared: 1) assuming a dose of $1 \times 10^{11}$ AAV vector expressing a transgene to treat blindness administered to the eye, up to 400,000 doses could be generated in a single

| Resin | Order Information | Reference | AAV serotype |
|---|---|---|---|
| Poros 50HS | Applied Biosystems, PN 1-3359-07 | http://www3-appliedbiosystems-com/cms/groups/psm_support/documents/generaldocuments/cms_041648-pdf | AAV2 AAV6 |
| Poros 50HQ | Applied Biosystems, PN 1-2559-07 | http://www3-appliedbiosystems-com/cms/groups/psm_support/documents/generaldocuments/cms_041639-pdf | AAV1 AAV8 |
| Poros 50PI | Applied Biosystems, PN 1-2459-07 | http://www3-appliedbiosystems-com/cms/groups/psm_support/documents/generaldocuments/cms_041639-pdf | AAV5 |
| CHT Ceramic Hydroxyapatite | BioRad PN 1570041 | http://www-bio-rad-com/webroot/web/pdf/psd/literature/LIT611E-PDF | AAV9 |

Conditions can be reliably defined to achieve efficient AAV particle capture, removal of most non-vector impurities (i.e. washing away of impurities under conditions in which AAV particles remain bound to the resin), and then elution of AAV particles. Following recovery from the chromatography step(s), the purified AAV particles (i.e. bona fide AAV vectors, empty capsids, and other vector related impurities) can be concentrated by tangential flow filtration, typically to a concentration in the range between $1 \times 10^{12}$ to $1 \times 10^{16}$ AAV particles per milliliter (corresponding approximately to 0.1 to 100 milligrams per milliliter), using elevated ionic strength buffers (Wright et al (2005) *Mol* gradient run; 2) assuming a dose of $1 \times 10^{12}$ AAV vectors expressing a transgene for Parkinson's Disease administered to CNS, up to 40,000 doses could be generated in a single gradient run; 3) assuming a dose of $1 \times 10^{14}$ AAV vectors expressing a transgene for hemophilia, administered to the liver, up to 400 doses could be generated in a single gradient run. We predict that AAV particles could be further concentrated 10 fold (to $10^{16}$ AAV particles per mL—corresponding to approximately 100 mg/mL, a concentration of biologic material that is routinely achieved for other biomolecules such as monoclonal antibodies) prior to the gradient ultracentrifugation step, and that this high but reasonably achievable concentration would result in 10-fold higher yields of bona fide vector from each standard ultracentrifugation run (capable of processing approximately 400 mL per batch), i.e. up to $4 \times 10^{17}$ vector genomes. Furthermore, larger scale ultracentrifugation machines could reasonably be expected to process at least 10-fold larger volumes of concentrated AAV particles, resulting at least $4 \times 10^{18}$ vector genomes (i.e. $4 \times 10^{18}$ highly purified, bona fide AAV vectors), the latter corresponding to 40,000 doses of $1 \times 10^{14}$ vector genomes per human subject with hemophilia B. These calculations indicate that the cesium chloride ultracentrifugation step, when performed in the novel purification platform described herein, is readily amenable to scale-up to meet all anticipated needs for manufacture of AAV vectors. Unexpectedly, at least according to the currently conventional bioprocess industry belief that gradient ultracentrifugation is not scalable, the novel bioprocessing steps (and importantly their order of performance) indicates that gradient ultracentrifugation step is not the limiting step in AAV vector purification.

Figure 1:
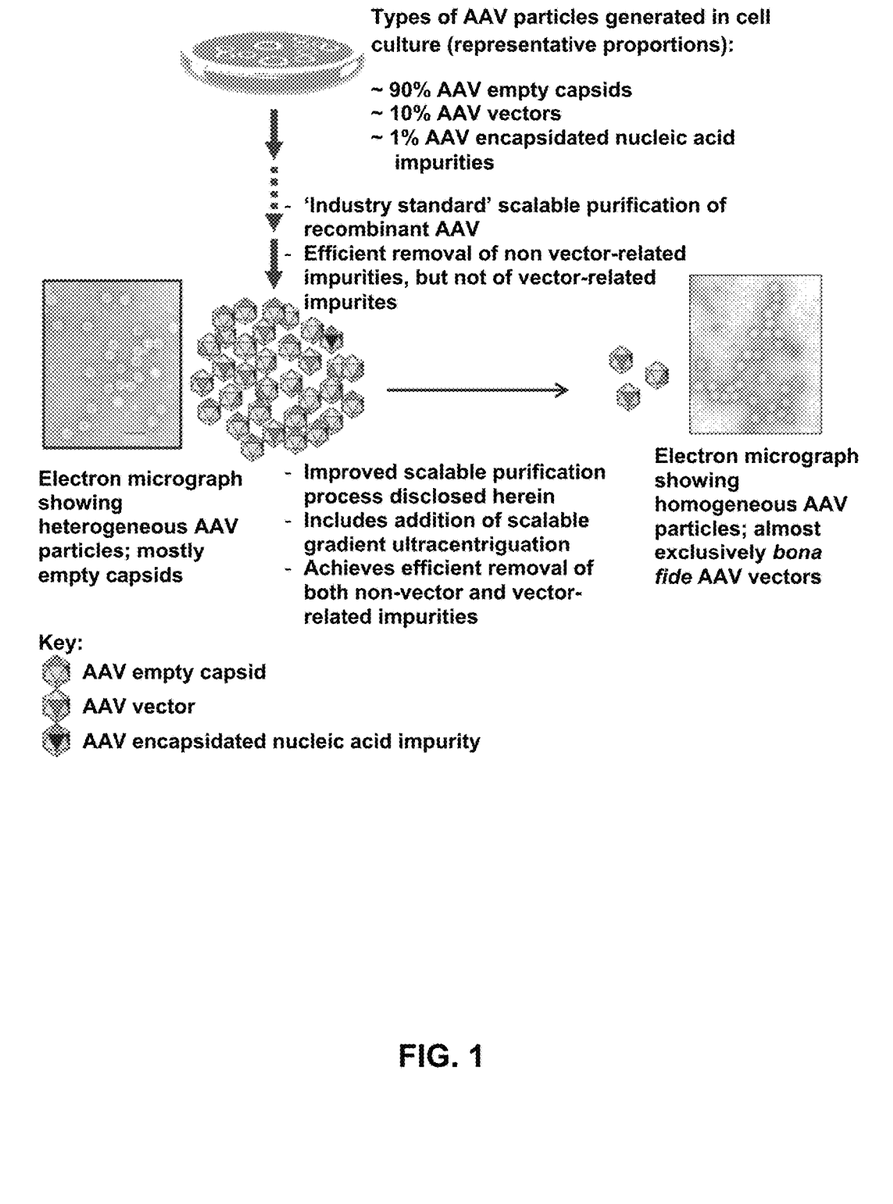
FIG. 1. Illustration of the types of AAV particles produced during generation of recombinant AAV, including schematic of purification achieved (a mixture of bona fide vector and vector related impurities) using current industry-standard scalable purification processes, and purification achieved (substantial removal of vector-related impurities) using our scalable purification method incorporating a gradient ultracentrifugation step that is rendered 'scalable' by virtue of sequence of purification steps used.
Figure 2:
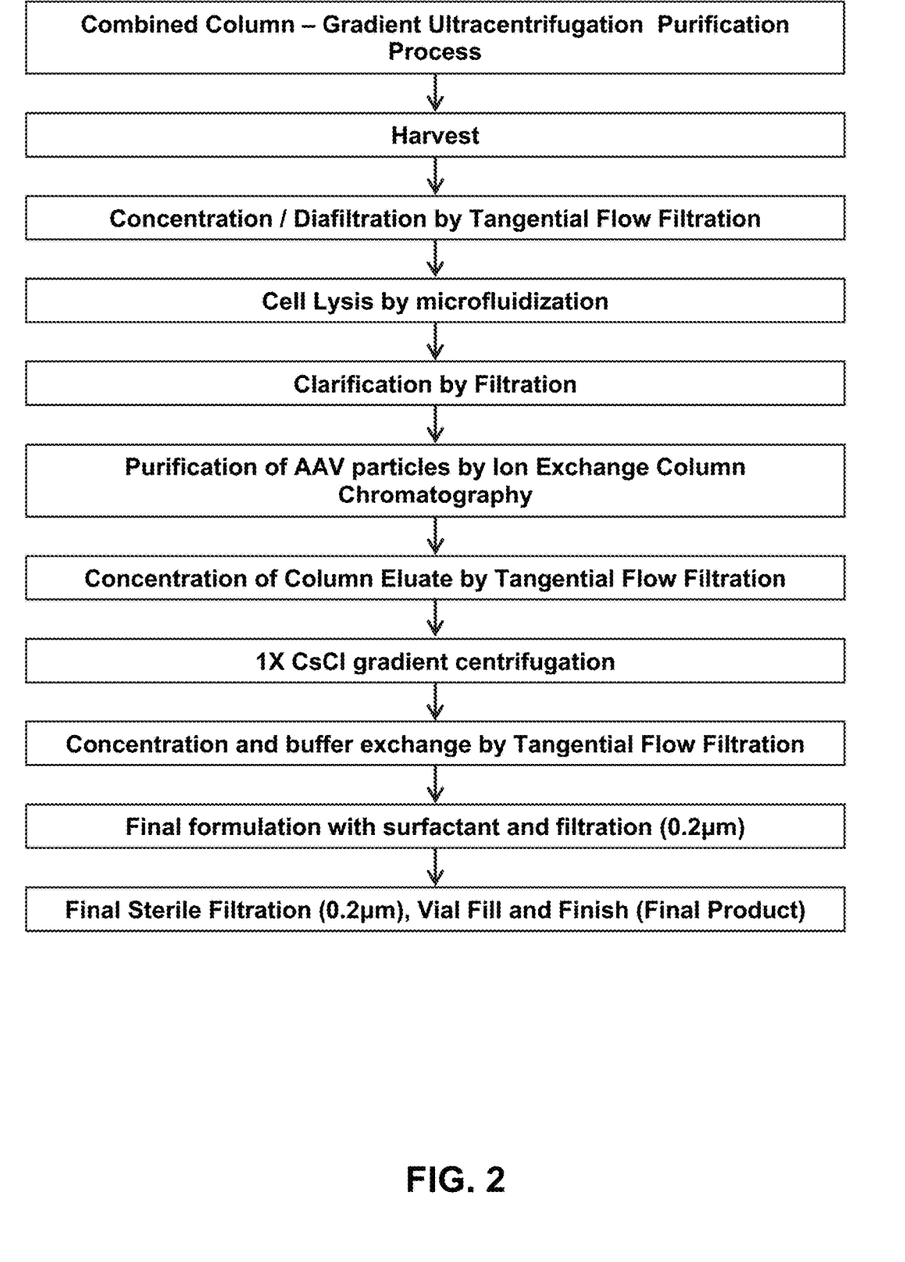
FIG. 2. Flow Chart showing vector purification process steps of the invention.
Figure 3A:
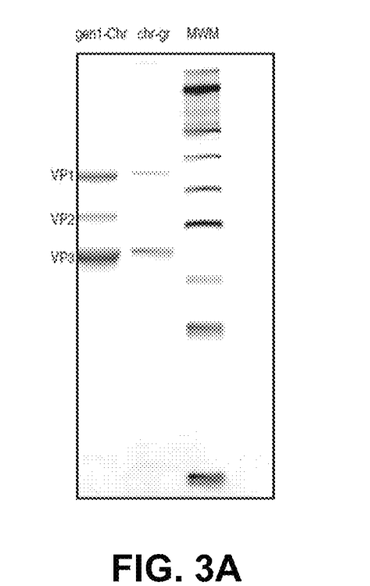
FIGS. 3A-3B. Analysis of representative industry-standard scalable purification process (gen1-Chr)-purified AAV vectors by gradient ultracentrifugation. The relative amounts and heterogeneity of AAV particles in apparently 'pure' vector, and the effectiveness of gradient ultracentrifugation in separation of bona fide AAV vector from vector-related impurities are shown. 'gen1-Che' is representative of current "industry-standard" scalable purification processes.
Figure 3B:
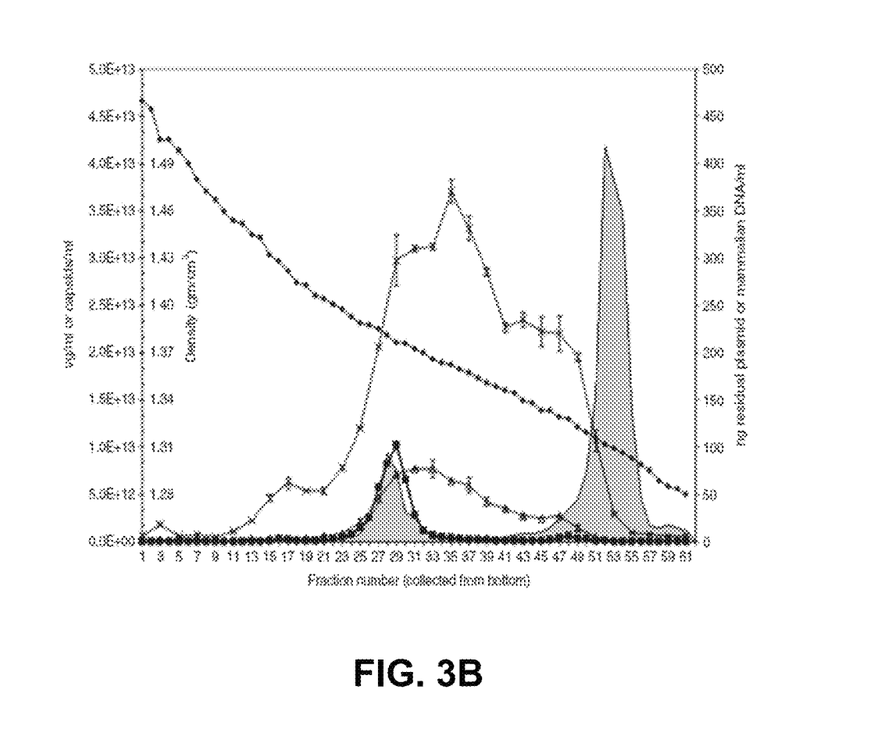
Figure 4:
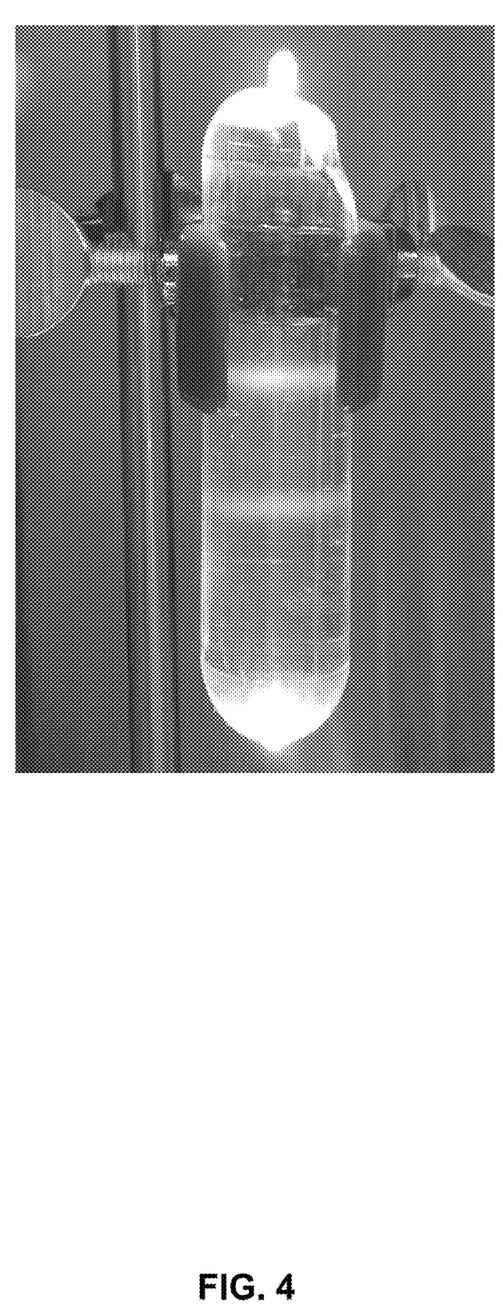
FIG. 4. A typical isopycnic gradient tube, with empty capsids, upper band, clearly separately from the low band, vector genome containing AAV vectors. The bands can be recovered separately, resulting in highly purified vectors and empty capsids.

One advantage of our purification process compared to currently used 'industry standard' scalable AAV vector purification processes is its ability to achieve higher purity via the inclusion of a step designed to efficiently remove product-related impurities. See FIGS. 1 and 2. The clinical significance of AAV capsid-specific immune responses is has been shown in studies by Manno et al. (2006: *Nature Med*), and the existence of abundant unnecessary excess capsid antigen (e.g. AAV empty capsids) and potentially immunostimulatory AAV encapsidated nucleic acids, i.e. vector related impurities, is described in the scientific literature (Smith et al (2003) *Mol Therapy* (abstract); Chadeuf et al (2005) *Mol Therapy*; European Medicines Agency (2005) *Report from the CHMP Gene Therapy Expert Group Meeting*; Hauck et al (2009) *Mol Therapy*). Data from other groups that generate and purify recombinant AAV at large scale for translation research and clinical product development is provided in FIG. 3 (from Hauck et al (2009) *Mol Therapy*).

EXAMPLE 2

An AAV vector (AAV2-hRPE65) purified using this method has been administered to patients and exhibited long-term efficacy in a clinical studies for Leber Congenital Amaurosis (Maguire et al (2008) *N Engl J Med*). Notably, similar AAV2-RPE65 vectors used by other groups purified by a manufacturing process that fails to remove vector-related impurities demonstrated significantly weaker evidence of efficacy, even when administered at higher doses (Bainbridge et al (2008) *N Engl J Med*, and Hauswirth et al (2008) *Human Gene Ther*).

Table 1 below provides a summary of this data.

TABLE 1

COMPARISON OF RESULTS OF RPE65-LCA CLINICAL TRIALS

| | Age at baseline (years)/gender | RPE65 mutation | Follow-up (months) | Anesthesia | Vector dose | Volume (ml) delivered | Injection location |
|---|---|---|---|---|---|---|---|
| | | | Current study | | | | |
| P1 | 24/M | E417Q/E417Q | 3 | L | $5.96 \times 10^{10}$ | 0.15 | M |
| P2 | 23/F | R44Q/R91W | 3 | L | $5.96 \times 10^{10}$ | 0.15 | ST |
| P3 | 21/M | Y368H/Y368H | 3 | L | $5.96 \times 10^{10}$ | 0.15 | T |
| | | | Bainbridge et al. | | | | |
| Patient 1 | 23/M | Y368H/Y368H | 12 | G | $1.0 \times 10^{11}$ | 1.0 | M |
| Patient 2 | 17/F | IVS1 + 5G>A/G40S | 12 | G | $1.0 \times 10^{11}$ | 1.0 | M |
| Patient 3 | 18/M | E6X/D167Y | 6 | G | $1.0 \times 10^{11}$ | 1.0 | M |
| | | | Maguire et al. | | | | |
| Patient 1[b] | 26/F | E102K/E102K | 4.75 | G | $1.5 \times 10^{10}$ | 0.15 | SN |
| Patient 2[b] | 26/M | E102K/E102K | 2.75 | G | $1.5 \times 10^{10}$ | 0.15 | M |
| Patient 3 | 19/F | R234X/R234X | 1.25 | G | $1.5 \times 10^{10}$ | 0.15 | M |

| | Systemic immunosuppression | Ocular complications reported | Entry visual acuity (study eye) | Post-treatment visual acuity | Considered significant visual acuity change | Patient vision in dim lighting (self-report) |
|---|---|---|---|---|---|---|
| | | | Current study | | | |
| P1 | No | FT | 20/240[a] | 20/317 | No | + |
| P2 | No | No | 20/195[a] | 20/138 | No | + |
| P3 | No | No | 20/283[a] | 20/191 | No | + |
| | | | Bainbridge et al. | | | |
| Patient 1 | Yes | No | 20/286 | 20/145 | No | NC |
| Patient 2 | Yes | No | 20/662 | 20/662 | No | NC |
| Patient 3 | Yes | No | 20/115 | 20/115 | No | + |
| | | | Maguire et al. | | | |
| Patient 1[b] | Yes | No | <20/2000 | 20/1050 | Yes | + |
| Patient 2[b] | Yes | MH | <20/2000 | 20/710 | Yes | + |
| Patient 3 | Yes | No | 20/640 | 20/290 | Yes | + |

Abbreviations: LCA, Leber congenital amaurosis; L, local; G, general anesthesia; M, macula including fovea; ST, superotemporal retina; SN, superonasal retina; T, temporal retina; MH, macular hole; FT, foveal thinning; NC, no change; NM, not measured; +, patient-reported improvement.
[a]Average of two baseline measures. Refractive errors: P1 = −0.25 + 1.50 × 090; P2 = −1.50 + 0.50 × 075; P3 = −2.70 + 1.75 × 100.
[b]Fraternal twins.

The AAV2 vector, AAV2.hRPE65v2 contains the 1.6 kb human RPE65 cDNA4-6 with a modified Kozak sequence engineered at the translational start site. The cDNA is under control of a hybrid chicken β actin (CBA) promoter. AAV2-hRPE65 (specifically, AAV2-hRPE65v2) was manufactured using appropriate current Good Manufacturing Practices (cGMP) at the Children's Hospital of Philadelphia using the vector purification method reported herein. In particular, AAV2-RPE65 was generated by transient transfection of HEK293 cells. The harvested cells and cell culture supernatant was concentrated by tangential flow filtration using 100 kDa Molecular Weight cutoff hollowfiber membranes. The concentrated harvest was subjected to three rounds of microfluidization to lyse cells and release AAV particles. The cell lysate was subjected to filtration (using a Sartorius 0.2 micron filter cartridge) and the clarified cell lysate was subjected to cation exchange column chromatography using Poros 50HS resin. Specifically, the clarified cell lysate was applied to the resin in neutral buffered saline at a salt concentration of approximately 200 mM NaCl, washed (i.e. the resin subjected to solutions that remove impurities, but not bound AAV particles) with a neutral buffered saline solution containing 5 mM sarkosyl (a surfactant) at a salt concentration of approximately 100 mM NaCl, further washed with a neutral buffered saline solution to remove residual sarkosyl, incubated in a neutral buffered salt solution containing a nuclease (Benozonase) at a concentration of 100 Units/mL to digest and remove nucleic acid impurities, and further washed with a neutral buffered saline solution to remove residual nuclease. Finally AAV particles were eluted using a neutral buffered saline solution at a salt concentration of approximately 400 mM NaCl, providing sufficiently elevated ionic strength to disrupt binding of AAV particles from the chromatography resin. The purified AAV particles eluated from the cation exchange chromatography column were supplemented with high purity cesium choride salt to a final concentration corresponding to a density of approximately 1.35 gm/mL, filtered through a sterile 0.2 micron membrane, and then subjected to isopynic ultracentrifugation at 50,000 rpm using a fixed angle rotor in a laboratory scale Beckman Ultracentrifuge. Post centrifugation, visible bands corresponding to AAV2-RPE65 were recovered from each centrifuge tube using sterile needles and syringes. Collected bands corresponding to AAV2-RPE65 were pooled and subjected to diafiltration by tangential flow filtration using 100 kDa molecular weight cutoff hollowfibers, resulting in removal of cesium chloride from the AAV2-RPE65 vectors containing solution The vector was then formulated into 180 mM NaCl, 20 mM sodium phosphate, and 0.001% Pluronic F68 (also known as Poloxamer 188), pH7.3. These vectors, appropriately diluted, were administered to human subjects lacking an integral form of the human RPE65 gene (and therefore suffering from Leber congenital amaurosis, a form of blindness). The benefits realized by the human subjects that received these vectors have been reported by Maguire et al (2008, 2009) and by Simonelli et al (2009). Two other teams concurrently performed clinical studies with AAV2-RPE65 (i.e. recombinant AAV2 vectors containing the gene for human RPE65), and the results of their studies have been reported. These other teams purified their AAV2-RPE65 vectors by a purification method that utilized column chromatography, but lacked the gradient ultracentrifugation step. As summarized by Hauswirth et al (2008), AAV2-RPE65 prepared using the method reported herein (i.e. the platform AAV vector purification method that incorporates both column chromatography and gradient ultracentrifugation, the steps combined in a manner to render the gradient ultracentrifugation scalable), was administered in the low doses to human subjects (approximately 4-fold to 7-fold lower than the doses administered to humans by the other two teams) yet gave rise to the best result. In particular, the best significant improvement in visual acuity (3 out of 3, see table 1) was observed by Maguire et al (2008). In contrast, Bainbridge et al (0 out of 3) and Hauswirth et al (0 out of 3) both reported no significant improvement in visual acuity in any of the subjects treated by them. Although other factors may contribute to the differences observed in these clinical trials, it is clear that the AAV2-RPE65 purification method used for the trial reported by Maguire et al was a significant factor accounting for the superior efficacy observed.

The vector used in this study was modified to optimize delivery to target cells by two mechanisms: 1) the addition of surfactant to the final formulation to prevent binding of vector to the injection device, an important consideration given the relatively low doses of vector delivered and 2) elimination of vector related impurities which insures that every vector particle taken up by the target cells has the potential to result in RPE65 expression. Standard vector preparations, purified without a step to remove empty capsid, are typically >80% empty capsid, while the preparation used in these studies is >95% full capsid.

As mentioned above, all three patients with LCA2 who received AAV2.hRPE65v2 by subretinal injection showed evidence of improvement in retinal function. Improvement in the pupillary light reflex by objective physiological testing was accompanied by improved values in subjective psychophysical measures. Testing revealed gains in visual acuity at 6 weeks; thereafter, there was a slower rate of improvement. Reduction in nystagmus, such as the reduction we previously reported in canine studies, may account for the improved visual acuity in the left (uninjected) eye of Patient 2. The improvements in the eyes that received injection exceeded the limits of test-retest variability and were of a magnitude believed to be of functional importance.

There were no apparent local or systemic adverse events elicited by exposure to the AAV vector. The macular hole that developed in the right eye of patient 2 two weeks after subretinal injection did not appear to be related to AAV2.hRPE65v2 administration, since no signs of inflammation or acute retinal toxicity were observed. We hypothesize that the macular hole was caused by contraction of a preexisting membrane stimulated by the surgical procedure, although it is possible that it was a direct result of the surgical procedure itself. Whereas the development of a macular hole would not be expected to affect retinal function in patients with a loss of central vision similar to that of our patients, it could critically affect the vision of those with a lesser degree of retinal degeneration.

The clinical benefit to the patients has been sustained during the 6 months since the experimental treatment of LCA2 in Patient 1. Clearly, the improved purification process described herein, which removes empty capsids from the formulation to be administered contributed to this clinical benefit.

While the invention has been described in detail and with reference to specific examples thereof, it will be apparent to one skilled in the art that various changes and modifications can be made therein without departing from the spirit and scope thereof.

What is claimed is:

1. A method for producing a highly purified adeno-associated (AAV) vector formulation said method comprising the steps of:

(a) harvesting cells comprising recombinant AAV vector particles;
(b) concentrating said cells harvested in step (a) via tangential flow filtration to produce a concentrated harvest;
(c) lysing said concentrated harvest produced in step (b) to produce a lysate;
(d) filtering said lysate produced in step (c) to produce a clarified lysate;
(e) subjecting said clarified lysate produced in step (d) to ion exchange column chromatography to produce a column eluate comprised of purified AAV vector particles, and optionally concentrating said column eluate by tangential flow filtration to produce a concentrated column eluate;
(f) mixing said column eluate or said concentrated column eluate produced in step (e) with cesium chloride to produce a mixture, and subjecting said mixture to gradient ultracentrifugation to substantially separate said bona fide AAV vector particles from empty capsid AAV vector particles and other AAV vector related impurities;
(g) collecting said bona fide AAV vector particles separated in step (f) and subjecting said collected bona fide AAV vector particles to a buffer exchange by tangential flow filtration;
(h) formulating said bona fide AAV vector particles resulting from step (g) with surfactant to produce an AAV vector formulation; and
(i) filtering said AAV vector formulation produced in step (h) to produce a highly purified AAV vector formulation in which at least 90% of the AAV vector particles in said highly purified AVV vector formulation are bona fide AAV particles.

2. A method for producing a highly purified AAV vector formulation according to claim 1, wherein said bona fide AAV vector particles of the eluate of step (e) are present at a concentration of about 100 mg/mL.

3. A method for producing a highly purified AAV vector formulation according to claim 1, wherein said bona fide AAV vector particles are present in said highly purified AAV vector formulation produced in step (i) at a concentration of $10^{15}$ particles per mL.

4. A method for producing a highly purified AAV vector formulation according to claim 1, wherein said bona fide AAV vector particles are present in said highly purified AAV vector formulation produced in step (i) at a concentration of $10^{16}$ particles per mL.

5. A method for producing a highly purified AAV vector formulation according to claim 1, wherein said bona fide AAV vector particles are present in said highly purified AAV vector formulation produced in step (i) at a concentration of $10^{17}$ particles per mL.

6. A method for producing a highly purified AAV vector formulation according to claim 1, wherein said bona fide AAV vector particles are derived from an AAV selected from the group consisting of AAV1, AAV2, AAV5, AAV6, AAV8 and AAV9.

7. An AAV vector particle formulation comprising bona fide AAV vector particles purified using the method of claim 1 in a pharmaceutically acceptable carrier, and wherein the AAV particles in the formulation are present at a concentration of at least $10^{15}$ particles per mL.

8. A method for producing a highly purified AAV vector formulation according to claim 1, wherein said bona fide AAV particles comprise a transgene that encodes a nucleic acid selected from the group consisting of a siRNA, an antisense molecule, miRNA a ribozyme and a shRNA.

9. A method for producing a highly purified AAV vector formulation according to claim 1, wherein said bona fide AAV particles comprise a transgene that encodes a gene product selected from the group consisting of insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), TGFβ, activins, inhibins, bone morphogenic protein (BMP), nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, netrin-1 and netrin-2, hepatocyte growth factor (HGF), ephrins, noggin, sonic hedgehog and tyrosine hydroxylase.

10. A method for producing a highly purified AAV vector formulation according to claim 1, wherein said bona fide AAV particles comprise a transgene that encodes a gene product selected from the group consisting of thrombopoietin (TPO), interleukins, monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand, IgG, IgM, IgA, IgD and IgE, chimeric immunoglobulins, humanized antibodies, single chain antibodies, T cell receptors, chimeric T cell receptors, single chain T cell receptors, class I and class II MHC molecules.

11. A method for producing a highly purified AAV vector formulation according to claim 1, wherein said bona fide AAV vector particles comprise a transgene encoding a protein useful for correction of in born errors of metabolism selected from the group consisting of carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor V, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, RPE65, H-protein, T-protein, a cystic fibrosis transmembrane regulator (CFTR) sequence, and a dystrophin cDNA sequence.

12. A method for producing a highly purified AAV vector formulation according to claim 11, wherein said transgene encodes Factor VIII or Factor IX.

13. A method for producing a highly purified AAV vector formulation according to claim 1, comprising collecting the empty capsid fraction separately in step (f).

14. A method for producing a highly purified AAV vector formulation according to claim 1, wherein said empty capsids are present in said filtrate of step (i) in an amount of 10% or less.

15. A method for producing a highly purified AAV vector formulation according to claim 1, wherein said bona fide AAV vector particles are present in said filtrate of step (i) in an amount of at least 95%.

16. A method for producing a highly purified AAV vector formulation according to claim 14, wherein said empty capsids are present in said filtrate of step (i) in an amount of 5% or less.

17. A method for producing a highly purified AAV vector formulation according to claim 1, wherein said centrifugation in step (f) is conducted in a single step.

18. A method for producing a highly purified AAV vector formulation according to claim 1, wherein said centrifugation in step (f) is density gradient ultracentrifugation.

19. A method for producing a highly purified AAV vector formulation according to claim 1, wherein said column eluate in step (e) is concentrated by tangential flow filtration to produce a concentrated column eluate.

20. A method for producing a highly purified AAV vector formulation according to claim 1, further comprising adding a nuclease to the lysate produced in step (c).

21. A method for producing a highly purified adeno-associated (AAV) vector formulation, said method comprising the steps of:
   (a) harvesting cells comprising recombinant AAV vector particles;
   (b) concentrating said cells harvested in step (a) via tangential flow filtration to produce a concentrated harvest;
   (c) lysing said concentrated harvest produced in step (b) to produce a lysate;
   (d) filtering said lysate produced in step (c) to produce a clarified lysate;
   (e) subjecting said clarified lysate produced in step (d) to ion exchange column chromatography to produce a column eluate comprised of purified AAV vector particles, and optionally concentrating said column eluate by tangential flow filtration to produce a concentrated column eluate;
   (f) mixing said column eluate or said concentrated column eluate produced in step (e) with cesium chloride to produce a mixture;
   (g) subjecting said mixture in step (f) to gradient ultracentrifugation conducted in a single step to substantially separate said bona fide AAV vector particles from empty capsid AAV vector particles and other AAV vector related impurities;
   (h) collecting said bona fide AAV vector particles separated in step (g) and subjecting said collected bona fide AAV vector particles to a buffer exchange by tangential flow filtration;
   (i) formulating said bona fide AAV vector particles resulting from step (h) with surfactant to produce an AAV vector formulation; and
   (j) filtering said AAV vector formulation produced in step (i) to produce a highly purified AAV vector formulation in which at least 90% of the AAV vector particles in said highly purified AVV vector formulation are bona fide AAV particles, and wherein said bona fide AAV vector particles are present in said highly purified AAV vector formulation at a concentration of $10^{15}$ particles per mL.

22. A method for producing a highly purified AAV vector formulation according to claim 1, further comprising in step (a) harvesting cells and cell culture supernatant comprising recombinant AAV vector particles and in step (b) concentrating said cells and said cell culture supernatant.

23. A method for producing a highly purified AAV vector formulation according to claim 21, further comprising in step (a) harvesting cells and cell culture supernatant comprising recombinant AAV vector particles and in step (b) concentrating said cells and said cell culture supernatant.

24. A method for producing a highly purified AAV vector formulation according to claim 1, wherein said bona fide AAV particles comprise a transgene that encodes a gene product selected from the group consisting of interleukin-1 through interleukin-17.

* * * * *

UNITED STATES PATENT AND TRADEMARK OFFICE
CERTIFICATE OF CORRECTION

PATENT NO. : 10,328,145 B2
APPLICATION NO. : 15/081001
DATED : June 25, 2019
INVENTOR(S) : John Fraser Wright et al.

Page 1 of 1

It is certified that error appears in the above-identified patent and that said Letters Patent is hereby corrected as shown below:

In the Specification

At Column 1 after the "GOVERNMENT SUPPORT" section, please amend Lines 17 to 21, as follows:
--This invention was made with government support under Grant No. HHSN268200748203C awarded by the National Institutes of Health. The government has certain rights in the invention.--

Signed and Sealed this
Seventh Day of April, 2020

Andrei Iancu
*Director of the United States Patent and Trademark Office*